(12) United States Patent
Hultgren

(10) Patent No.: US 6,217,334 B1
(45) Date of Patent: *Apr. 17, 2001

(54) DENTAL SCANNING METHOD AND APPARATUS

(75) Inventor: Bruce Willard Hultgren, Victoria, MN (US)

(73) Assignee: Iris Development Corporation, Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/789,918

(22) Filed: Jan. 28, 1997

(51) Int. Cl.[7] .................................................. A61C 11/00
(52) U.S. Cl. ............................................ 433/215; 433/214
(58) Field of Search .................................... 433/213, 214, 433/215, 223

(56) References Cited

U.S. PATENT DOCUMENTS

| | | |
|---|---|---|
| 4,182,312 | 1/1980 | Mushabac ............................... 433/68 |
| 4,611,288 | 9/1986 | Duret et al. . |
| 4,752,964 | 6/1988 | Okada et al. . |
| 4,827,909 | 5/1989 | Kato et al. . |
| 4,935,635 | 6/1990 | O'Harra . |
| 5,017,139 | 5/1991 | Mushabac ............................ 433/109 |
| 5,027,281 | 6/1991 | Rekow et al. . |
| 5,071,252 | 12/1991 | Matsuura . |
| 5,121,333 | 6/1992 | Riley et al. . |
| 5,121,334 | 6/1992 | Riley et al. . |
| 5,124,524 | 6/1992 | Schuster et al. . |
| 5,128,870 | 7/1992 | Erdman et al. . |
| 5,184,306 | 2/1993 | Erdman et al. . |
| 5,198,877 | 3/1993 | Schulz . |
| 5,224,049 | 6/1993 | Mushabac . |

(List continued on next page.)

FOREIGN PATENT DOCUMENTS

PCT/US91/
02458   10/1991  (WO) .

OTHER PUBLICATIONS

"OTP for Windows" ; Website: http://www.webworld-inc.com/orthovision/OTPBrochure.htm; Jul. 31, 1996.
"Treat Your Patients With Care"; Website: http://www.sib-worldinc.com/orthovision/treatwithcare.htm; Jul. 31, 1996.
"Ortho–Vision Technoilogies"; Website: http:www.web-worldinc.com/orthovision/News 1Q96.htm; Jul. 31, 1996.
"Digital Record Keeping"; Website: http://www.webworld-inc.com/orthovision/RecordsBrochure.htm; Jul. 31, 1996.
"Welcome to Ortho–Vision"; Website: http://www.web-worldinc.com/orthovision/ ; Jul. 31, 1996.

*Primary Examiner*—Ralph A. Lewis
(74) *Attorney, Agent, or Firm*—Merchant & Gould PC

(57) ABSTRACT

A dental and soft tissue scanning method and system is disclosed which uses fast laser line scanning techniques of negative image impressions, whereby an array of electronic data is generated. In operation the array of negative image scan data is generated by a scanner 60 and provided to a processor 501. The negative image scan data may be saved in a memory device 504 as a permanent record of the baseline condition of the patient's teeth, or temporarily prior to one of several other options. The processor 501 may convert the data to a positive image for display on the video display unit 503 for teaching or educational purposes with the patient. Alternatively, the positive information data may be transmitted to a remote PC 505 for storage, study by a consulting dentist (or physician), or fabrication of a study cast by fabrication device 507. These and other options may be selected by the user of computer 500 via the input device 506. The programming operation of the processor 501 provides for scanning each of the upper and lower impressions and the bite registration impression. These scans provide the information necessary to create an electronic equivalent of a physical study cast.

15 Claims, 8 Drawing Sheets

U.S. PATENT DOCUMENTS

| | | |
|---|---|---|
| 5,257,184 | 10/1993 | Mushabac . |
| 5,257,203 | 10/1993 | Riley et al. . |
| 5,273,429 | 12/1993 | Rekow et al. . |
| 5,343,391 | 8/1994 | Mushabac . |
| 5,347,454 | 9/1994 | Mushabac . |
| 5,432,703 | 7/1995 | Clynch et al. . |
| 5,448,472 | 9/1995 | Mushabac . |

DENTAL SCANNING METHOD AND APPARATUS

FIELD OF THE INVENTION

The present invention relates generally to a system of dental modeling and imaging which creates digital images of teeth topography; and more particularly relates to scanning a dental impression wherein a set of negative image electronic data of the patient's teeth and surrounding soft tissue is created which can be electronically manipulated, displayed, stored and transmitted for uses relating to creating dental appliances and diagnosis, among others.

BACKGROUND OF THE INVENTION

Dental study casts are an integral part of a dentist's understanding of how a patient's teeth and bite function in a static relationship. This static relationship serves three important functions. The primary function is one of a diagnostic function for interpretation of any discrepancies or problems that exist within the bite relationship. The second function is educational. For example, the study casts provide better communication as a concrete model while helping the patient understand any discrepancies that may exist in the way their teeth function in that static relationship. Third, the dental study casts serve an important medical/legal function in defining the pre-existing static bite relationship prior to the performance of any work. This work can be defined either from an oral surgical standpoint, prosthetic standpoint or orthodontic/periodontal standpoint.

Significant complications are associated with study casts, however, since the casts need to be stored for an extended period (generally seven years). For example, the storage of the study casts requires large amounts of space in humidity controlled environments, as well as extensive laboratory procedures involving OSHA guidelines and space utilization for the study casts to be constructed. In addition, a significant amount of turn-around time is required for the curing process of the plastic study casts to occur. In light of these significant constraints as well as the importance associated with having an accurate recording of the pre-existing bite relationship, there arises a need for an apparatus (or system) and method in which electronic image data can be collected from an impression to circumvent the need for storage of physical study casts.

Prior to discussing a summary of the present invention, however, detailed discussions of the construction of a working model (study cast) of the teeth and other prior art devices will be presented.

As noted above, in order to study dental work to be performed on a patient's teeth, a working model of the teeth constructed of a plaster study cast is created. The plaster cast is based on a series of impressions taken to obtain the geometry of the teeth. To take an impression, alginate impression material is poured into a tray (i.e., an impression tray) which is then introduced into the patient's mouth for a period of time (typically one to two minutes). The impression material sets about the teeth and soft tissues forming a negative impression. The patient also bites into a soft material for registering a simultaneous imprint of the upper and lower teeth which records the relationship of the teeth in the upper and lower jaws respectively in three planes of space.

Once the impressions have set, they are sent to a lab to be processed into an upper and lower plaster study cast. The study casts are articulated together via the bite registration material to reproduce the bite of the patient. After construction, the study casts are returned to the dentist/orthodontist as a working study cast.

A serious drawback of this method is the number of labor intensive steps required to produce the study casts, the space and legal storage requirements of the study casts, and the inability to interface the study casts interactively with other diagnosis information (e.g., photographs and radiographs). Accordingly, if additional work is required, the cast fails in some way or is damaged, and/or the cast is lost, then an additional impression series must be taken. Therefore, there also exists a need in the art to develop a set of electronic data from the series of dental impressions wherein only a single impression need be taken for multiple interactive functions.

In the past, several devices have been designed for the electronic imaging of teeth. Also, other devices are known which utilize numerical data to create prototype devices. While known examples of such systems and devices follow, generally such systems do not provide the accuracy required for orthodontic work. Instead, such systems are generally useful only for crowns, fillings, etc.

U.S. Pat. No. 4,182,312 generally discloses a dental probe having a stylus which is connected through a rod to a three position transducer. Three signals are produced for indicating the position of the probe at any point to which the probe is applied. The transducers are mounted on an index tray which is adapted to be fastened to the jaw of the patient. Thus the patient's jaw becomes the origin against which all measurements are made. Contact between the tip of the stylus and the patient's tissue completes a circuit to turn on a recording mechanism which receives the transducer's outputs.

U.S. Pat. No. 4,611,288 generally discloses a method of producing dental prostheses (e.g., crowns, inlays, dentures and the like) using an optical impression taken of the oral region with nontraumatic radiation. The reflected waves are transformed into numerical data which is used to operate a numerically controlled machine in the fabrication process.

U.S. Pat. No. 4,752,964 generally discloses an apparatus for producing, from an object having a three-dimensional shape, a shape equivalent or analogous to the three-dimensional shape. Here, light is irradiated to the object in an optical cutting plane. The light is picked up by an image pick-up device, and two-dimensional positions of the light are obtained in a direction perpendicular to the optical cutting plane to determine its three dimensional shape.

U.S. Pat. No. 4,935,635 generally discloses a three-dimensional point measuring system which includes a laser diode for projecting a triangulating beam at a surface to be mapped, with the beam scanned repeatedly across the surface. Photodetectors detect the position of the beam as reflected from the mapped surface, given by triangulation Z-axis or depth information. Correlation of a particular point with the position of the scanner along the scan line gives Y-axis information, or information in a width direction. The scanner and diode are mounted on a slide or platform device which moves perpendicularly to the Y axis in the direction in an out of the mouth, driven by a stepper motor, and the monitored position of the stepper motor is coordinated with the other information on each spot to yield X-axis information.

U.S. Pat. No. 5,198,877 generally discloses a method and apparatus for optically sampling numerous points on the surface of an object to remotely sense its shape utilizing two stages. The first stage employs a moveable non-contact scanner, which in normal operation sweeps a narrow beam of light across the object, illuminating a single point of the object at any given instant in time. The location of that point relative to the scanner is sensed by multiple linear photo-detector arrays behind lenses in the scanner. These sense the location by measuring the relative angular parallax of the point. The second stage employs multiple fixed but widely separated photoelectronic sensors, to detect the locations of several light sources affixed to the scanner. Individual light sources are distinguished by time-multiplexing their on-off states. A coordinate computer calculates the absolute spatial positions where the scanner light beam is incident on the object to generate a computer model.

U.S. Pat. No. 5,224,049 discloses a method for use in preparing a dental prosthesis and U.S. Pat. No. 5,347,454 generally discloses a system for use in preparing a dental prosthesis.

U.S. Pat. No. 5,448,472 discloses a method for collecting three-dimensional surface information in dental applications via a video camera. A tape strip is applied to a tooth surface to provide a distance reference or standard for use by a computer in analyzing the video data to determine actual distances. The tape strips are additionally provided with identification markings identifying the type of surfaces and the teeth to which the tape strips are attached.

Each of the foregoing systems, devices and methods suffer the drawback in that bulky, expensive specialized devices are required. The processes are extremely time consuming or require the introduction of devices into the patient's mouth for extended periods of time or which leads to patient discomfort. Also, these systems are limited to dental restorative procedures only. Reduced accuracy and precision of the measurements also greatly limit the usefulness of these systems to direct scanning of the dental impressions, study casts or both.

Therefore, there arises a need for a cost effective, relatively fast, and efficient system and method for electronically scanning dental surfaces or dental materials such that the resulting data may be manipulated for a wide variety of dental and/or medical purposes and uses.

SUMMARY OF THE INVENTION

The present invention provides an improved dental and soft tissue scanning method and system, using fast laser line scanning techniques whereby an array of electronic data is generated. The electronic data which is generated may be used for a number of purposes including visual display, storage of a patient base-line, creation of one or more study casts, and transmission to a remote location for analysis, among others. The elimination of the requirement to routinely construct study casts is also accomplished. The principles of the present invention may be utilized in connection with the scanning of other parts of the human body for later analysis, as well as diagnosis and construction of appliances, braces and other dental applications. Therefore, while the present invention is described in connection with the taking of an impression of a patient's teeth and surrounding soft tissues, any number of other applications may exist.

In a preferred embodiment of a method and system constructed according to the principles of the present invention, there is provided several components which comprise the system. These components include a set of fixtured dental impression trays, a fixtured clutch device to record the bite registration, a tool for holding the dental impression tray(s), a scanner device, and a processor operatively connected to the scanner for receiving the data from the scanner device. Preferably the processor takes the negative image data and converts the data to a positive three dimensional image for display, transmission, conversion to CNC (Computer numeric control) data for prototyping, etc. Optionally, the image data may also be taken from a study cast. Further, such data may optionally be stored as negative image data and retrieved for use at a later date (e.g., in the event that additional positive reproductions are desired or required to be constructed).

Therefore according to one aspect of the invention, there is provided, a method of generating a set of electronic data from a dental impression or study cast, comprising the steps of: forming a dental impression of a patient's teeth and surrounding soft tissue; mounting the dental impression or study cast in a fixture; scanning the impression with a laser device along 3 axes, wherein a set of electronic data is developed which corresponds to the impression.

A further aspect of the present invention is the method as recited above, wherein the electronic data is constructed as a negative image of the patient's teeth and surrounding soft tissue. Yet another aspect of the present invention includes the step of converting the negative image data to a set of positive three dimensional image data for analysis.

These and other advantages and features which characterize the present invention are pointed out with particularity in the claims annexed hereto and forming a further part hereto. However, for a better understanding of the invention, reference should be had to the following drawing and detailed description.

BRIEF DESCRIPTION OF THE DRAWING

Referring to the drawing, wherein like numerals represent like parts throughout the several views.

DETAILED DESCRIPTION

A detailed discussion of the various devices comprising a preferred embodiment system will be deferred pending a discussion of the overall method steps used to practice the present invention.

1. Overview

Figure 1:
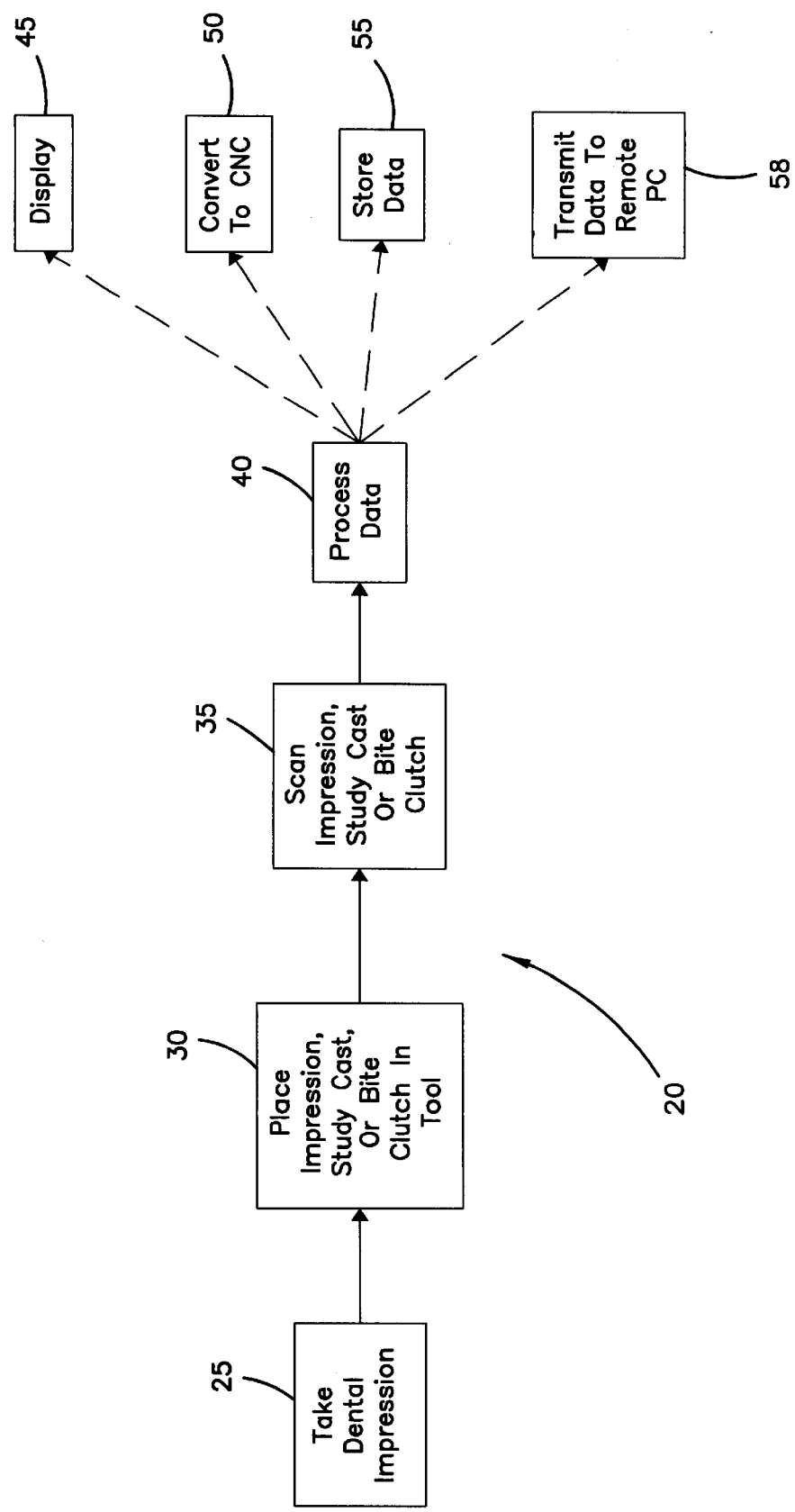
FIG. 1 illustrates the method steps 20 used to practice the principles of the present invention.
Figure 2A:
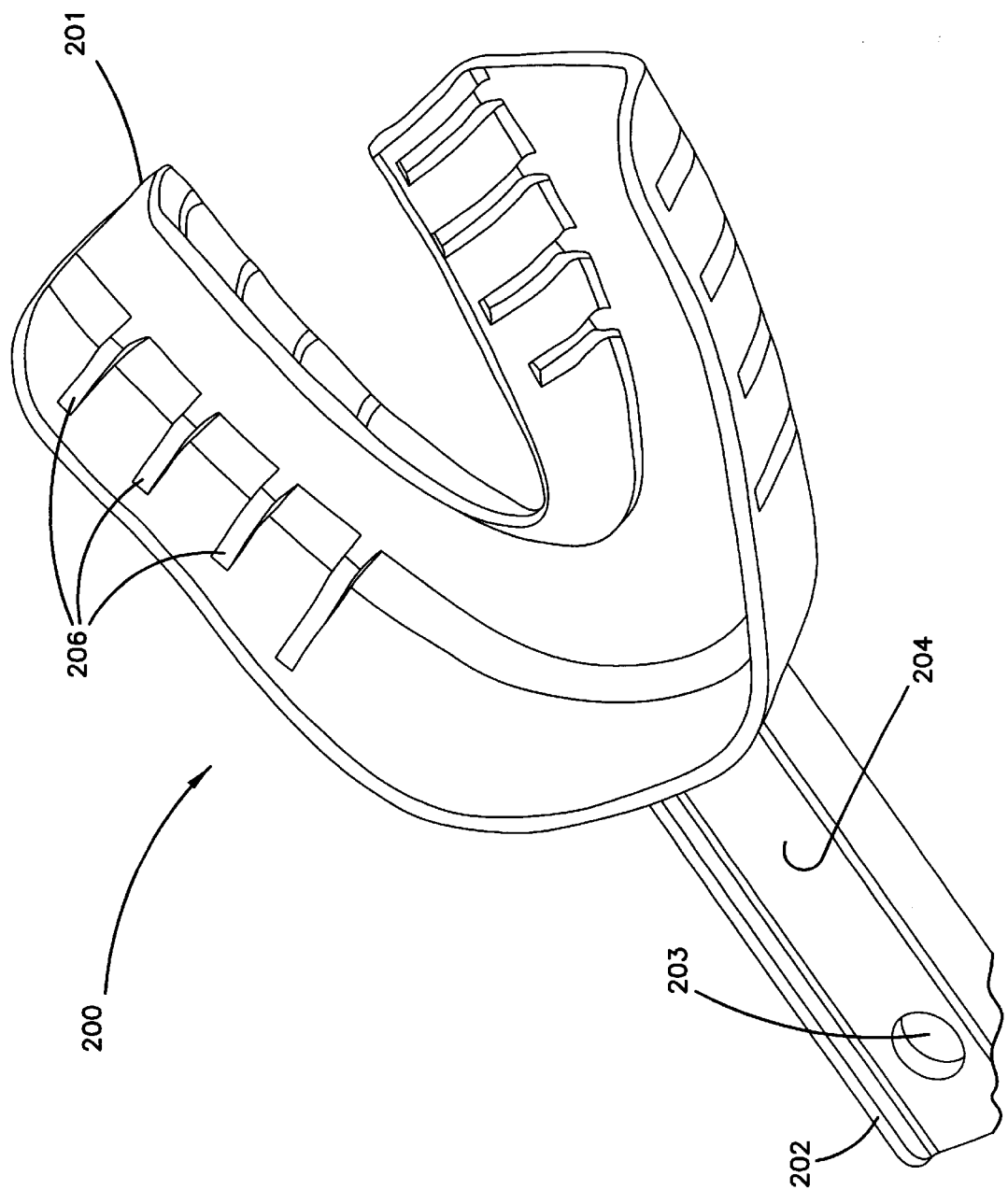
FIGS. 2a and 2b illustrate perspective views of lower 200 and upper 220 impression trays, respectively, used in connection with the present invention..
Figure 2B:
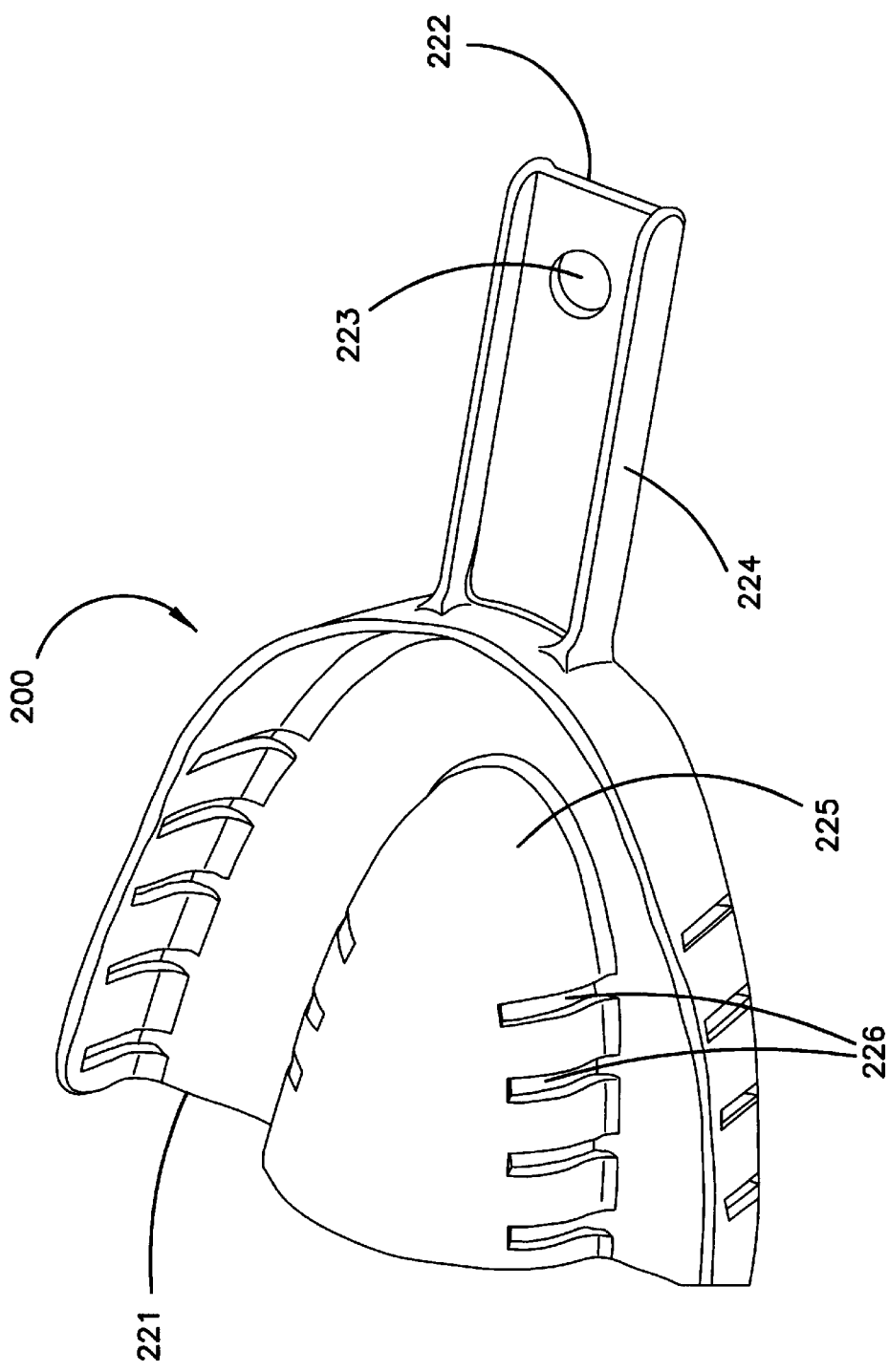
Figure 3A:
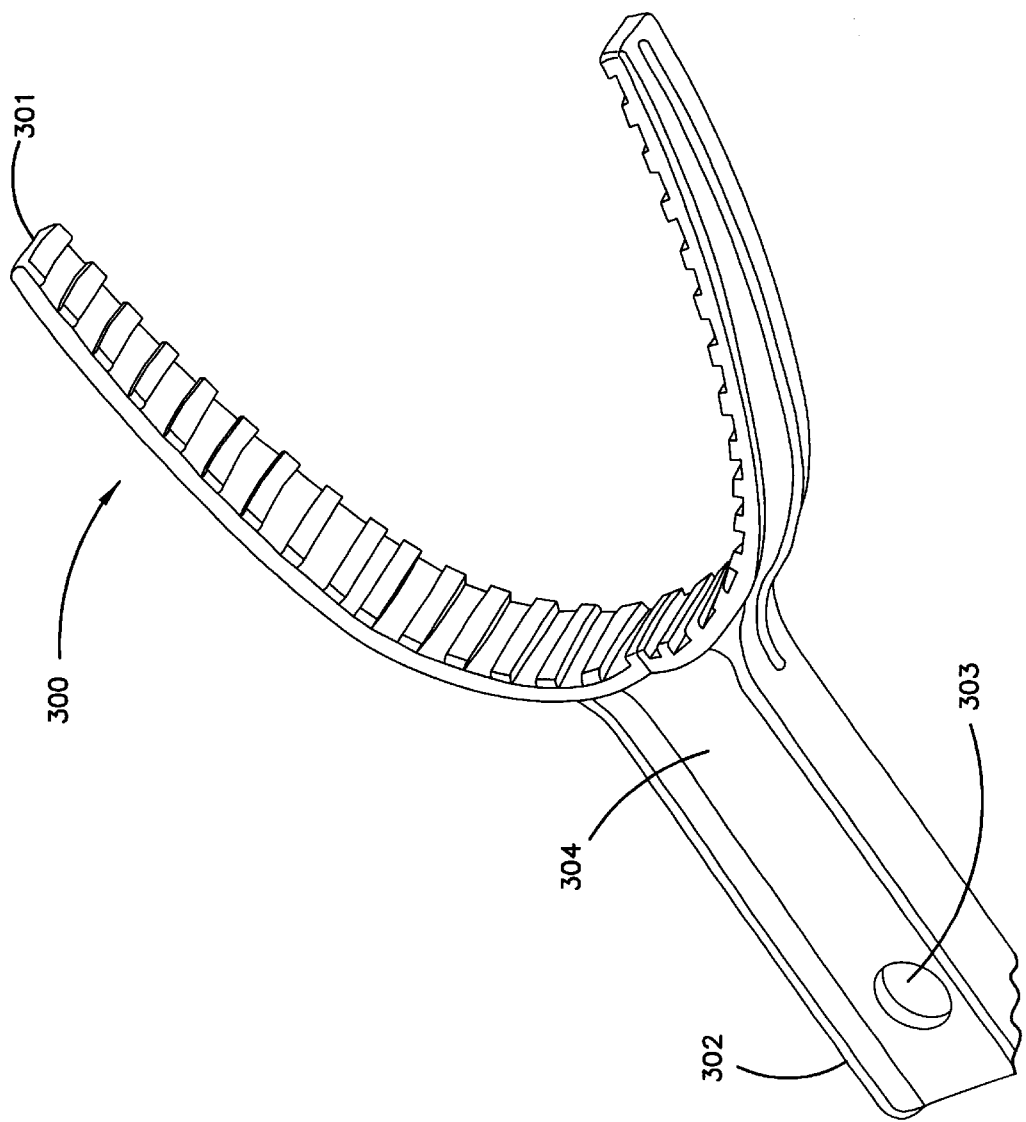
FIG. 3a illustrates a perspective view of a registration tray 300 used in connection with the present invention.
Figure 3B:
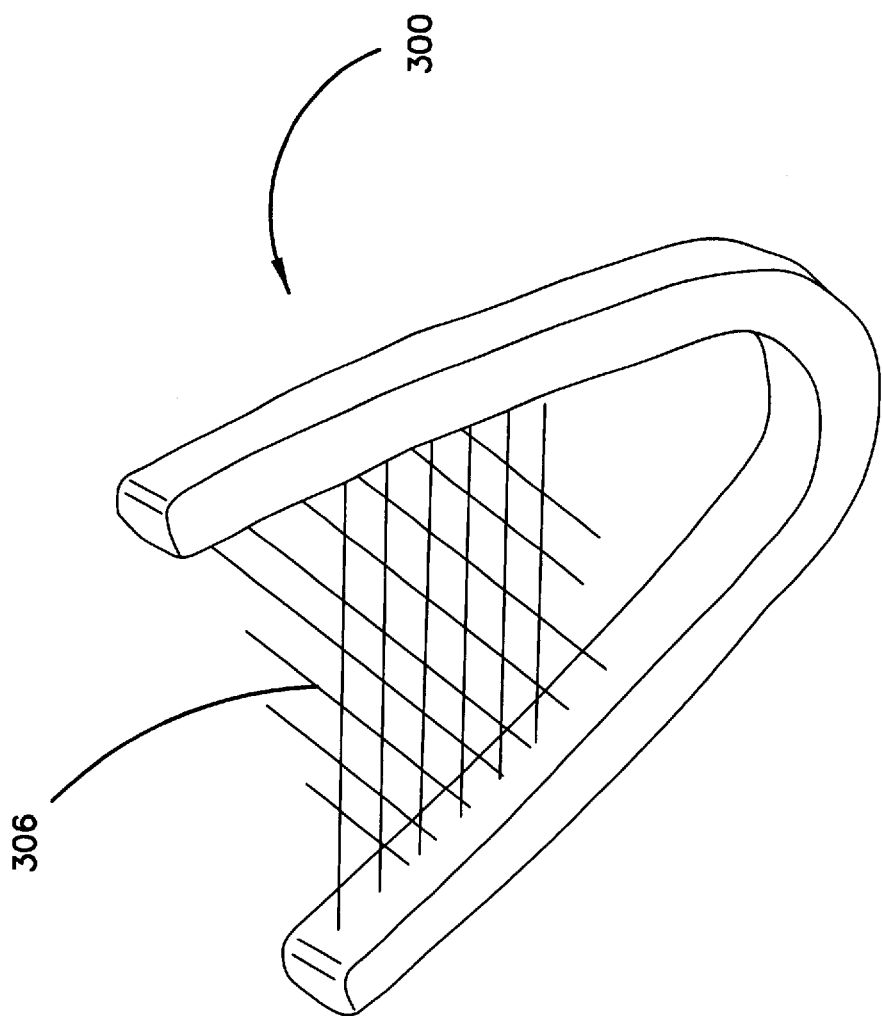
FIG. 3b diagrammatically illustrates the preferred arrangement and configuration of the impression material retaining mesh 306 used in connection with tray 300.

Referring first to FIG. 1, the overall method of the present invention is illustrated generally by the designation 20. First, at block 25, a dental impression of a patient's teeth and surrounding soft tissues (hereafter referred to collectively as "teeth" for convenience) is taken. The impression material hardens, forming a negative image of the teeth. The lower 200 and upper 220 trays used in connection with taking the impression are described below and are best seen in FIGS. 2a and 2b respectively. The bite/clutch tray 300 used in connection with determining the correct spatial orientation and relationship between the upper and lower impressions is described below and is best seen in FIGS. 3a and 3b.

At block 30, the impression tray 200 or 220 is placed in the tool or fixture 600 (described below and best seen in FIG. 5). The fixture 600 is used to securely hold the tray 200, 220, and/or 300 during the scanning step. The fixture 600 may also aid the scanning step by helping rotate the mold so that the image data can be properly generated. It will be appreciated that during this step at least one of the trays 200 and 220 include the hardened impression material which defines a negative image impression or mold of a patient's teeth.

Next at block 35, the scan of the impression occurs. In the preferred embodiment, a scanner manufactured by Laser Design Inc. of Minneapolis, Minn. designated as model number 8849648 may be used. The operation and scanning methodology used by this type of scanner is generally described in U.S. Pat. No. 5,124,524 (which is hereby incorporated herein by reference). Generally, the scanner model number 884648 manufactured by Laser Design is referred to as a line scanner device. It will be appreciated that for a complete study cast of the upper and lower teeth, two scans of the negative image impressions occur (i.e., one lower and one upper). Further, in order to properly reference the two sets of teeth together, a scan of the bite tray 300 impression also takes place.

Figure 6:
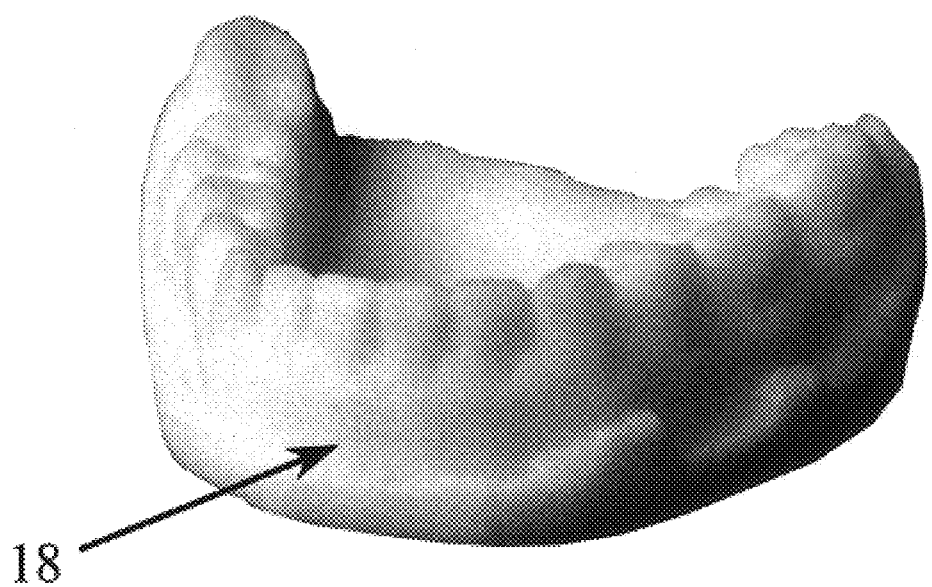
FIG. 6 is a perspective view of a positive image of a scanned portion of a study cast.

Referring now to FIGS. 1 and 6, at block 40 the image data is processed by processor 501. Such processing may include converting the negative image scan data into a positive image for display on a video display unit 503 (at optional block 45); converting the negative image scan data into CNC or other format of output for use by a fabrication device 507 (also known as a prototyping apparatus)(at optional block 50); storing the negative image scan data in a memory location or device 504 (at optional block 55); and/or transmitting the negative image scan data to a remote processor 505 via modem block 502 (at optional block 58).

In the preferred embodiment, one commercially available software package which may be used to generate three dimensional images from the line scan data is the package sold under the designation DataSculpt software available from Laser Design Inc. of Minneapolis, Minn.

2. Detailed Description of Components

Turning now to FIGS. 2a and 2b, the lower impression tray 200 and upper impression tray 220 are illustrated. The trays 200 and 220 are shown without impression material located thereon in order to more clearly illustrate the size and configuration of the respective trays. The trays 200 and 220 are generally horseshoe shaped with an elongate member 204 and 224 (respectively) integrally attached to and extending away from the arcuate portion of the horseshoe section. The elongate members 204 and 224 are generally within the same mean plane formed by the horseshoe section. However, those of skill in the art will appreciate that other locations and arrangements may be utilized. The upper tray 220 also includes a domed element 225 which is integrally formed and connects the interior portion of the horseshoe section of the tray 220.

Each of the trays 200 and 220 also includes a first end 201 and 221 (respectively) which is inserted into a patient's oral cavity during the process of taking the impression and a second end 202 and 222 (respectively) which includes a handle for helping insert and remove the trays. Located proximate the second ends 202 and 222 are holes 203 and 223 (respectively) which are arranged and configured to aid in the registration process of the scanning procedure (i.e., the holes 203 and 223 on the handles may be used in conjunction with the mounting fixture 600). However, including such holes 203 and 223 and/or using the holes in the registration process is optional.

Slots 206 and 226 are formed in the lower and upper trays 200 and 220 (respectively) to aid in the expansion of the impression material when a patient bites into the same, as well as helping retain the impression material on the tray 220 and 226 (and in a fixed manner) after removal from a patient's mouth and during scanning. Only several of the plurality of slots 206 and 226 are designated by the reference numerals in the Figures for the purpose of clarity. Also, those of skill in the art will appreciate that the number and arrangement of the slots 206 and 226 may be changed, with the slots 206 and 226 shown in FIGS. 2a and 2b being illustrative.

The trays 200 and 226 are preferably constructed by means of plastic injection molding process and of a material suitable for medical and dental purposes. Such material should also be selected to be rigid enough to hold the impression material in a stable fashion during scanning and be capable of being sanitized or sterilized.

Turning now to FIGS. 3a and 3b, the bite registration tray 300 is illustrated. Tray 300 is shown without impression material located thereon in order to more clearly illustrate the size and configuration of the tray. The tray 300 is generally horseshoe shaped with an elongate member 304 integrally attached to and extending away from the arcuate portion of the horseshoe section generally in the same mean plane formed by the horseshoe section,.

Tray 300 includes a first end 301 which is inserted into a patient's oral cavity during the process of taking the impression and a second end 302 which includes a handle for helping insert and remove the tray 300. Located proximate the second end 302 is hole 303 which is arranged and configured to aid in the registration process of the scanning procedure (i.e., the holes on the handles may be used in conjunction with the mounting fixture 600). However, including such hole 303 and/or using the hole in the registration process is optional.

FIG. 3b illustrates the bite tray 300 without the elongate member 304 and including an impression retaining mesh material 306 generally located within the horseshoe section. The material 306 is used to retain the impression material on the tray. It will be appreciated that this configuration allows a patient to bite into the impression material on either side of the mean plane formed by the horseshoe portion of tray 300 to register the upper and lower impressions relative to one another so that study casts, visual displays, etc. can be created with the proper spatial relationships. In the preferred embodiment, tray 300 is constructed in a manner similar to that described above in connection with trays 200 and 220.

Figure 5:
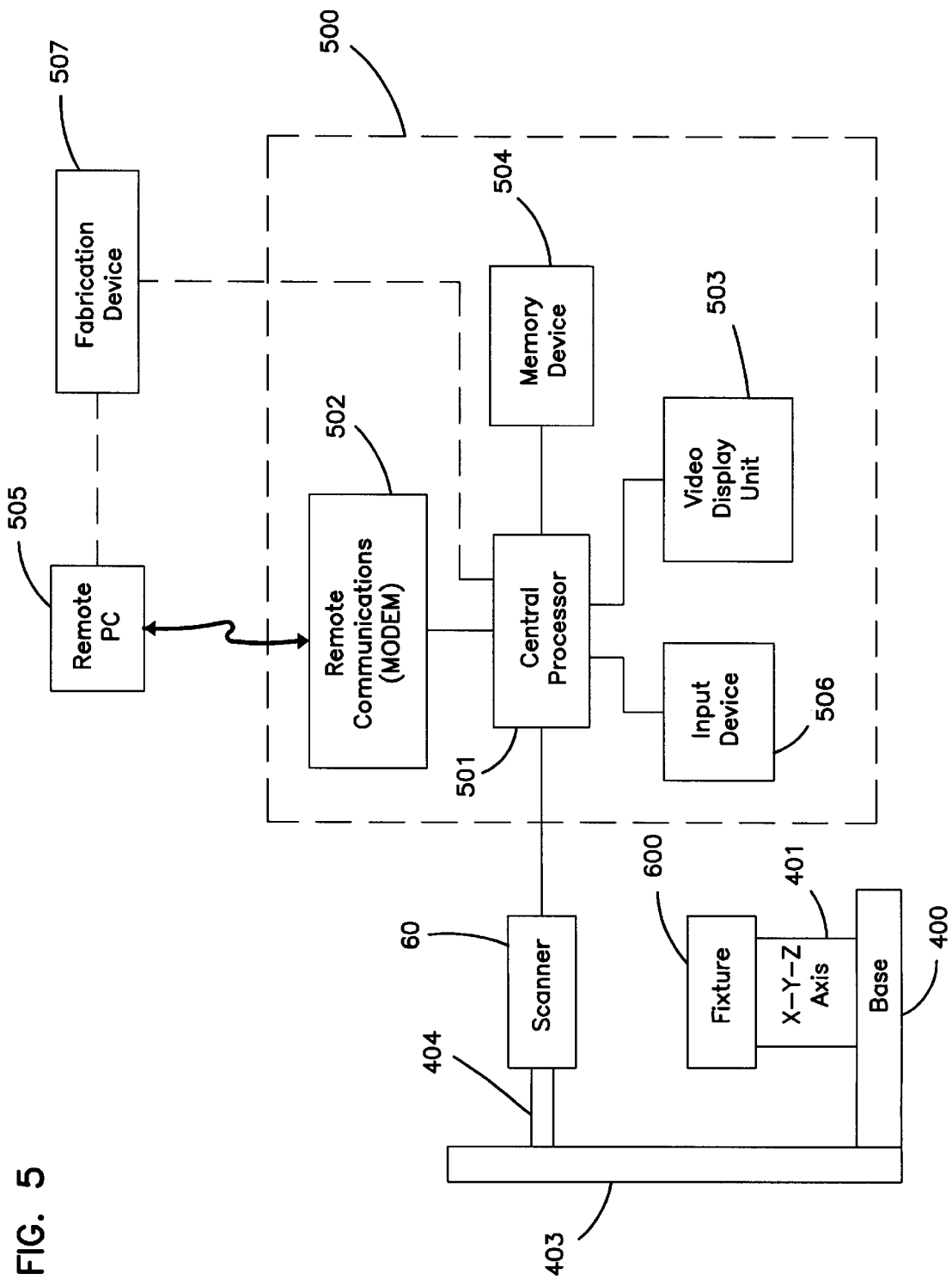
FIG. 5 diagramatically illustrates the functional blocks associated with the processor, memory, and remote computer associated with processing the data from the scanner 60.

The scanning tool or fixture 600 is best seen in FIG. 5. In the preferred embodiment, the fixture 600 is arranged and configured to securely hold the trays 200, 220, and 300 while rotating and/or moving on the fixture platform 402 (best seen in 4) as the array of negative image electronic data from the negative impression(s) is being generated by the scanner 60.

Figure 4:
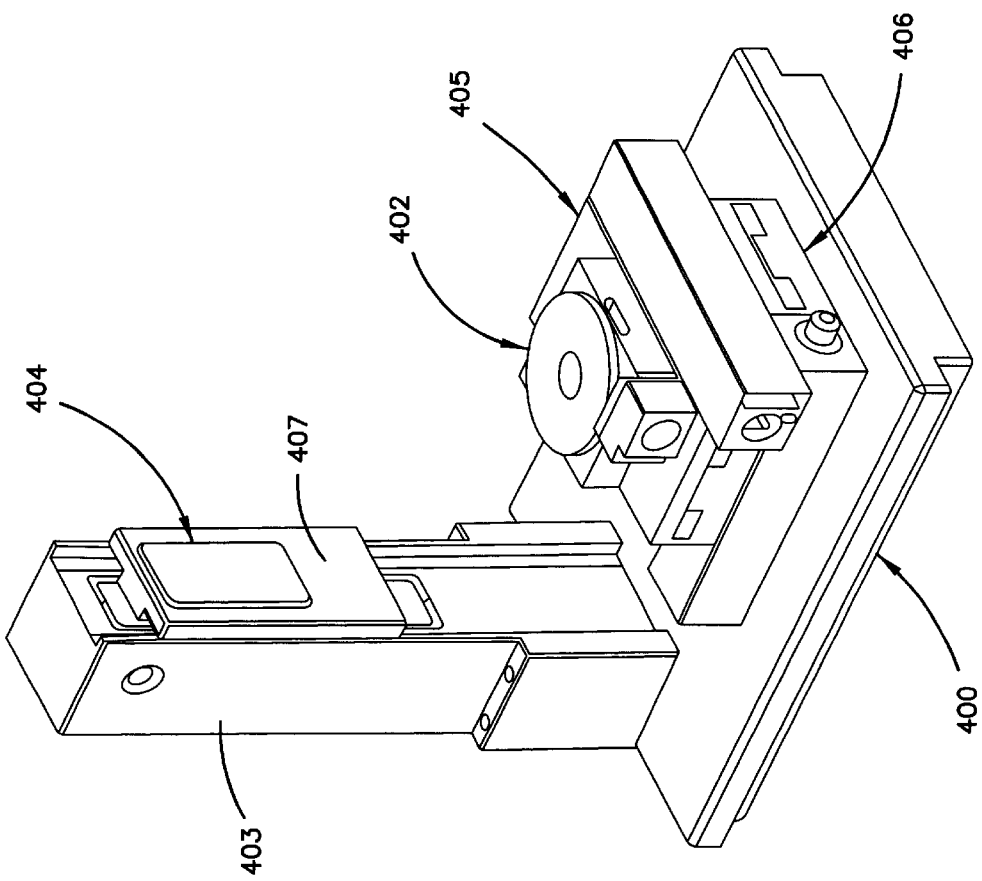
FIG. 4 illustrates a perspective view of a preferred embodiment base 400 and X-Y-Z axis devices 401 used in connection with scanner 60.

Referring to FIGS. 4 and 5, the scanner is designated generally at 60. As noted above, the scanner 60 and its operation is described in detail in U.S. Pat. No. 5,124,524. Also shown in FIG. 4 is the Z-axis column 407 which preferably provides precise vertical linear motion with a screw and nut assembly. Scanner mounting member 404 is operatively connected to the Z-axis column 407. Rotary stage 402 preferably provides precise rotational movement in the range of 0.001" quadrature resolution. X-axis stage 406 and Y-axis stage 405 provide X and Y coordinate control and preferably use lead screw assemblies. Column 403 is attached to base 400 and supports the scanner 60. In FIG. 5, the X axis stage 406, Y axis stage 405, the Z axis stage 407 and the rotational stage 402 are together referred to as block 401.

Still referring to FIG. 5, the functional blocks of the electronic components of the present invention are illustrated. The components include a computer 500 which preferably includes a processor 501, a video display unit 503, a memory device 504, a user input device 506 (e.g., a mouse and/or keypad), and a modem 502. Also illustrated is a remote computer 505, a fabrication device 507, and the scanner 60 (and its attendant X-Y-Z axis controllers and motors).

It will be appreciated by those of skill in the art that the computer 500 may be a personal computer (e.g., a Pentium based PC) or a special purpose computer. Further, the video display unit 503 may include any number of display devices such as cathode ray tubes, LCD displays, etc. Still further, the memory device 504 may include hard drives, floppy drives, magnetic tape, CD-ROM, random access memory, and read-only memory devices. Further, the modem 502 is illustrated to show a communications capability. Such capability may also be by way of a network, etc.

Fabrication device 507 may be connected directly to the computer 500 or may be connected to a remote computer 505. The fabrication device 507 may be any number of devices which can utilize computer generated data and create a three-dimensional object from such data. One example of such a machine are the devices utilizing stereo lithography technology manufactured by 3-D Systems of Valencia, Calif. under the model designations SLA-250 and SLA-500. Another example is the device utilizing filament technology (fused deposition modeling) manufactured by Statasys Corporation of Minneapolis, Minn. under the model designation FDM-1500.

In operation the array of negative image scan data is generated by the scanner 60 and provided to the processor 501. The negative image scan data may be saved in a memory device 504 as a permanent record of the baseline condition of the patient's teeth, or temporarily prior to one of several other options. For example, the data may be converted to a positive image and stored in that fashion as a permanent record of the baseline condition. Alternatively, the positive image may be displayed on the video display unit 503 for teaching or educational purposes with the patient. Still further, the positive information data may be transmitted to a remote PC 505 for storage, study by a consulting dentist (or physician), or fabrication of a study cast by fabrication device 507. The fabrication device 507 may optionally be connected directly to computer 500. These and other options may be selected by the computer 500 user via the input device 506.

The programming operation of the processor 501 provides for scanning each of the upper and lower impressions and the bite registration impression. These scans provide the information necessary to create an electronic equivalent of the prior art physical study casts. By using negative image impressions and a line scanner, high resolution and speed are gained wherein high quality study casts may be generated by a fabrication device 507 thereby replacing older methods of constructing the same. Although such fabricated casts may still be saved, since the data is generated and stored electronically, the problems associated with storage of prior art study casts may be reduced and/or eliminated. Further, the data may be used any number of times in different ways to accomplish a more robust practice.

It will be appreciated that the principles of this invention apply not only to the devices used to implement the invention, but also the method in general of generating an electronic array of dental impression scan image data from one or more negative impressions. For example, it is possible to scan existing study casts in order to generate an electronic data set and view the set in three dimensions as seen in FIG. 6 at the designation 18. By doing so, the image may be manipulated and/or stored as described above. Further, by doing so, the requirement to store existing study casts may be reduced or eliminated.

It is also contemplated that other impressions of a patient's body may be taken to form a negative image mold. The present invention may also be used to scan such negative images. A further extension of the present invention is to generate a direct scan image of teeth in a patient's oral cavity with a tool inserted in a patients mouth and provided to central processor 501.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefor other than as described herein can be configured within the spirit and intent of this invention. The system described herein is provided as only one example of an embodiment that incorporates and practices the principles of this invention. Other modifications and alterations are well within the knowledge of those skilled in the art and are to be included within the broad scope of the appended claims.

What is claimed is:

1. A method of generating a set of electronic data from a dental impression or study cast, comprising the steps of:
   a) forming a dental impression of a patient's teeth and surrounding soft tissue from either the teeth and surrounding soft tissue or from a study cast;
   b) mounting the dental impression in a fixture;
   c) scanning the impression with a laser line scanner device along three axes, wherein a set of electronic data is developed which corresponds to the impression or study cast.

2. The method of claim 1, wherein the electronic data is constructed as a negative image of the patient's teeth and surrounding soft tissue.

3. The method of claim 2, further comprising the step of converting the negative image data to a set of positive image data.

4. The method of claim 3, wherein the converting step is processed with a central processing unit.

5. The method of claim 3, further comprising the step of displaying the positive image data as a three dimensional output on a video display device.

6. The method of claim 1, further comprising the step of storing the electronic data in a computer memory location.

7. The method of claim 1, further comprising the step of fabricating orthodontic study casts, retention devices, and other dental applications from the electronic data using a fabrication device.

8. The method of claim 1, further comprising the steps of scanning a first impression of the lower teeth and soft tissue of a patient, scanning a second impression of the upper teeth and soft tissue of a patient, and scanning a third registration impression of the patient to spatially orient the first and second impressions relative to one another, wherein an array of negative image electronic data is generated of the complete teeth and soft tissue of a patient which is spatially oriented properly.

9. The method of claim 8, further comprising the step of fabricating orthodontic study casts, retention devices, and other dental applications from the array of negative image electronic data using a prototype device.

10. A method of generating a set of electronic data of the teeth and soft tissues inside of a human oral cavity from a dental impression, comprising the steps of:

a) scanning via a line scanner the impression or study cast along three axes to generate a plurality of scan data;
  b) creating a set of electronic data from the line scanner scan data which corresponds to the impression; and
  c) relating the line scanner scan data to each other, wherein the impression images of the teeth and soft tissues are accurately related to each other.

11. A system for generating a set of electronic data of the teeth and soft issues inside of a human oral cavity from a dental impression, comprising:

a) impression means for creating a negative impression mold of the teeth and soft tissue of a patient;
  b) fixture means for securely holding the impression means during movement of the impression;
  c) an X-Y-Z axis device arranged and configured for moving the fixture means;
  d) a line scanner for generating an array of negative image electronic data of the mold; and
  e) means for converting the array of negative image electronic data generated by the line scanner to an array of positive image electronic data.

12. The system of claim 11, wherein the positive image electronic data includes a first set of electronic data resulting from a scan of a patient's upper teeth and soft tissue, a second set of electronic data resulting from a scan of the patient's lower teeth and soft tissue, and a third set of electronic data resulting from a scan of a registration impression of the patient's upper and lower teeth and soft tissue.

13. The system of claim 11, wherein the converting means is a central processing unit.

14. The system of claim 11, further comprising the step of display means for displaying the positive image electronic data, wherein the electronic data may be visually perceived.

15. The system of claim 11, further comprising a memory device for storing the positive image electronic data.

* * * * *

UNITED STATES PATENT AND TRADEMARK OFFICE
CERTIFICATE OF CORRECTION

PATENT NO.    : 6,217,334 B1
DATED         : April 17, 2001
INVENTOR(S)   : Hultgren It is certified that error appears in the above-identified patent and that said Letters Patent is hereby corrected as shown below:

Title page,
Item [56], References Cited, U.S. PATENT DOCUMENTS, add
-- 5,338,198    8/1994    Wu et al.        433/213
5,452,219      9/1995    Dehoff et al.    433/223
5,549,476      8/1996    Stern            433/213 --
Item [56], References Cited, OTHER PUBLICATIONS,
"Technoilogies" should read -- Technologies --
Item [74], *Attorney, Agent, or Firm*, "Merchant & Gould PC" should read -- Merchant & Gould P.C. --

Column 2,
Line 58, "an" should read -- and --

Column 4,
Line 14, "3" should read -- three --
Line 38, delete extra "."
Line 47, "diagramatically" should read -- diagrammatically --

Column 6,
Line 31, "section,." should read -- section. --

Column 8,
Line 20, "patients" should read -- patient's --
Line 23, delete "that"

UNITED STATES PATENT AND TRADEMARK OFFICE
CERTIFICATE OF CORRECTION

PATENT NO. : 6,217,334 B1
DATED : April 17, 2001
INVENTOR(S) : Hultgren

It is certified that error appears in the above-identified patent and that said Letters Patent is hereby corrected as shown below:

Column 9,
Line 9, "prototype" should read -- fabrication --

Signed and Sealed this

Second Day of July, 2002

Attest:

JAMES E. ROGAN
Attesting Officer      Director of the United States Patent and Trademark Office